(12) United States Patent
Grissom

(10) Patent No.: US 7,913,320 B2
(45) Date of Patent: Mar. 29, 2011

(54) ADJUSTABLE IV CATHETER COVER DEVICE

(75) Inventor: Carolyn M. Grissom, Raleigh, NC (US)

(73) Assignee: Carolyn M. Grissom, Raleigh, NC (US)

( * ) Notice: Subject to any disclaimer, the term of this patent is extended or adjusted under 35 U.S.C. 154(b) by 751 days.

(21) Appl. No.: 11/893,595

(22) Filed: Aug. 16, 2007

(65) Prior Publication Data

US 2008/0045906 A1    Feb. 21, 2008

Related U.S. Application Data

(60) Provisional application No. 60/838,259, filed on Aug. 17, 2006.

(51) Int. Cl.
*A41D 27/12* (2006.01)
(52) U.S. Cl. .................................. 2/59; 602/3
(58) Field of Classification Search .................. 2/16, 20, 2/59; 128/877–879, 846; 602/3, 5, 20, 23
See application file for complete search history.

(56) References Cited

U.S. PATENT DOCUMENTS

| | | | |
|---|---|---|---|
| 3,741,203 A | 6/1973 | Liman | |
| 3,906,941 A | 9/1975 | Cook, Jr. | |
| 4,610,245 A | 9/1986 | Biearman | |
| 4,639,945 A | 2/1987 | Betz | |
| 4,951,317 A * | 8/1990 | Gray et al. | 2/16 |
| 5,063,919 A | 11/1991 | Silverberg | |
| 5,188,608 A | 2/1993 | Fritts | |
| 5,342,286 A | 8/1994 | Kelly et al. | |
| 5,392,786 A * | 2/1995 | Lewis et al. | 128/877 |
| 5,395,302 A | 3/1995 | Botha et al. | |
| 5,592,953 A | 1/1997 | Delao | |
| 5,605,534 A | 2/1997 | Hutchison | |
| 5,643,183 A | 7/1997 | Hill | |
| 5,720,713 A | 2/1998 | Hutchison | |
| 5,817,038 A * | 10/1998 | Orange et al. | 602/3 |
| 6,267,115 B1 | 7/2001 | Marshel | |
| 6,665,876 B1 * | 12/2003 | Newman | 2/59 |
| 7,662,116 B2 * | 2/2010 | Ritchey | 602/3 |

OTHER PUBLICATIONS http://www.showersleeve.com/ "The Perfect Shower Protector for IV's, PICC Lines, Casts and Bandages," Scottsdale, AZ, 2006.
Ten (10) Pictures illustrating the use of an earlier open fabric that can be formed into a cover for catheters attached to extremities (used as early as 2003).

* cited by examiner

*Primary Examiner* — Katherine Moran
(74) *Attorney, Agent, or Firm* — Jenkins, Wilson, Taylor & Hunt, P.A.

(57) ABSTRACT

Adjustable IV catheter cover devices are provided that include a sleeve defining a cavity therethrough. The sleeve can have first and second ends. First and second cuffs are integral to the sleeve at the respective first and second ends. The first cuff defines a first opening leading into the cavity and the second cuff defines a second opening leading into the cavity. The first and second cuffs each have an elastic portion, a fastening portion disposed next to a first end of the elastic portion, and a folding portion disposed between the elastic portion and the fastening portion. First and second fastening tabs are secured to the respective first and second cuffs at second ends of the respective elastic portions. The first and second fastening tabs are configured to engage the fastening portion of the respective cuffs to adjust the size of the respective first and second openings.

33 Claims, 11 Drawing Sheets

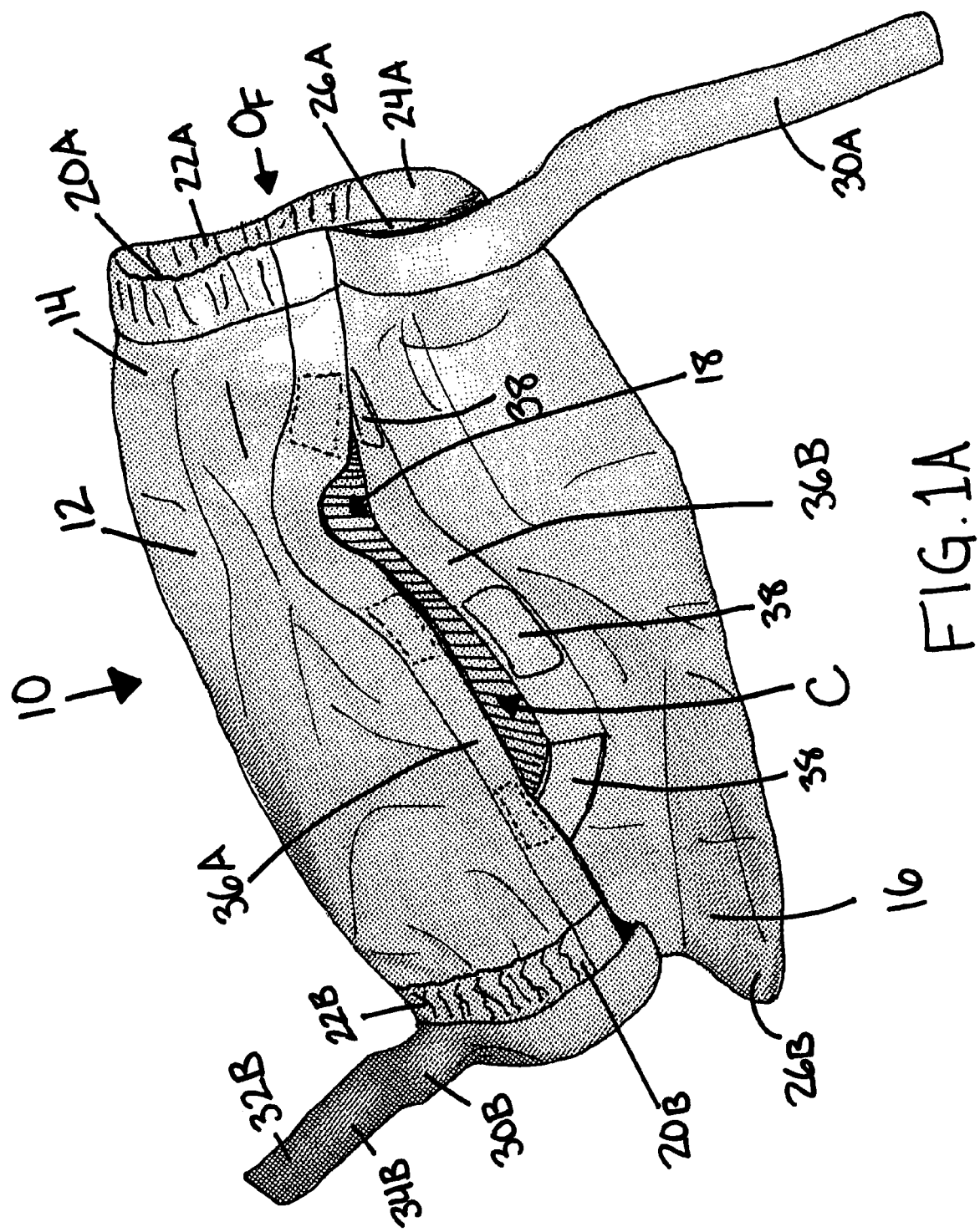

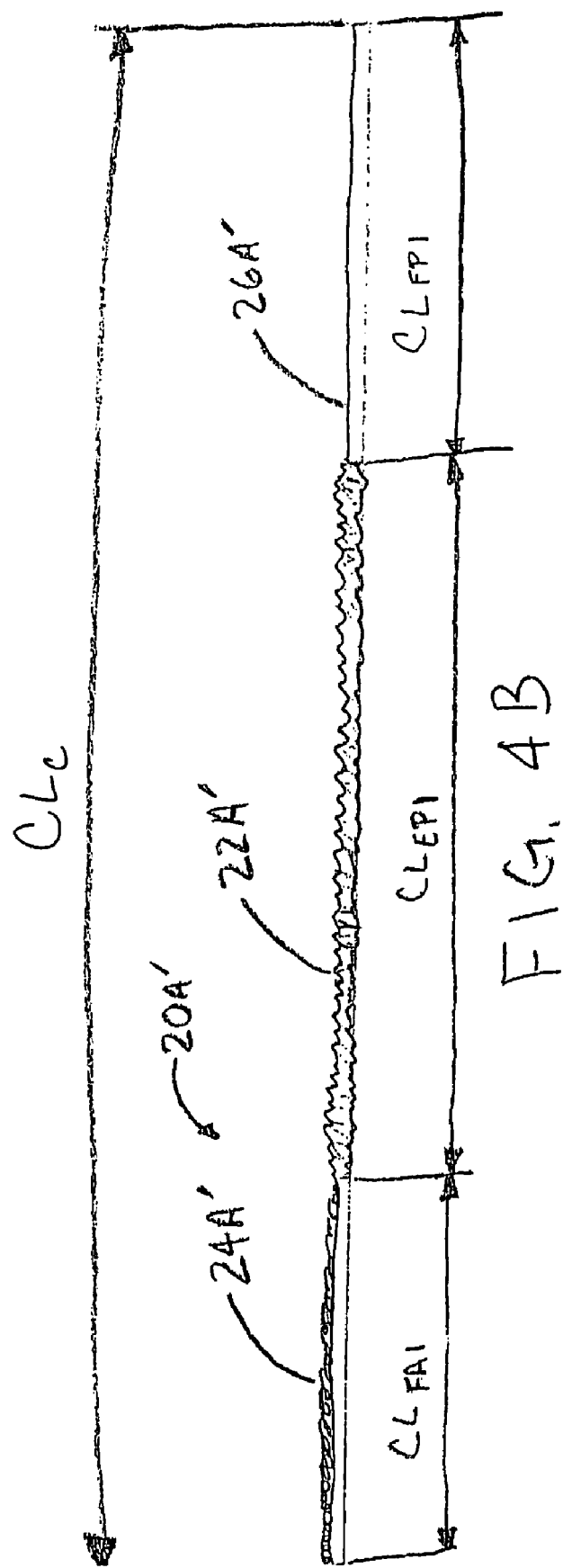

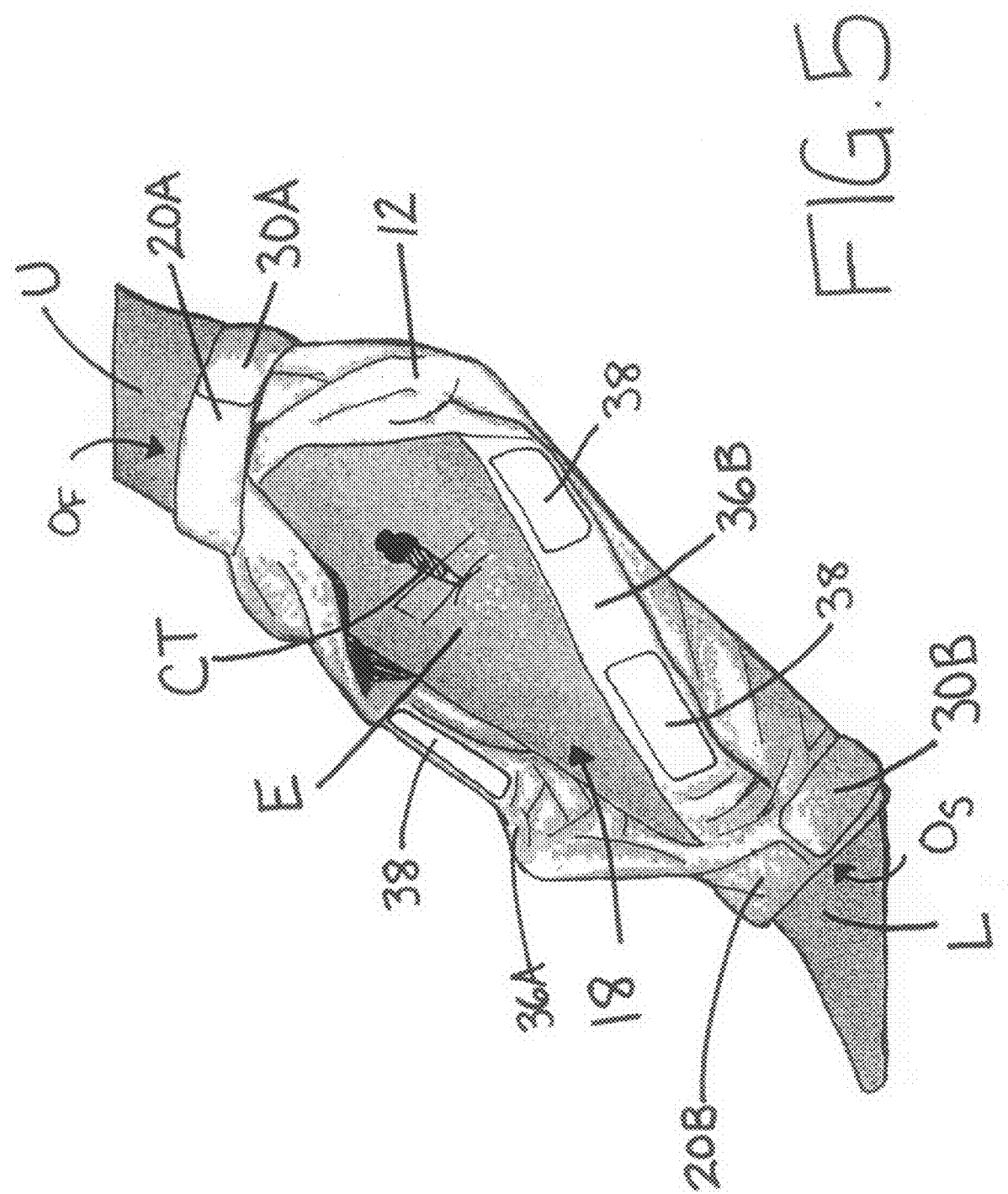

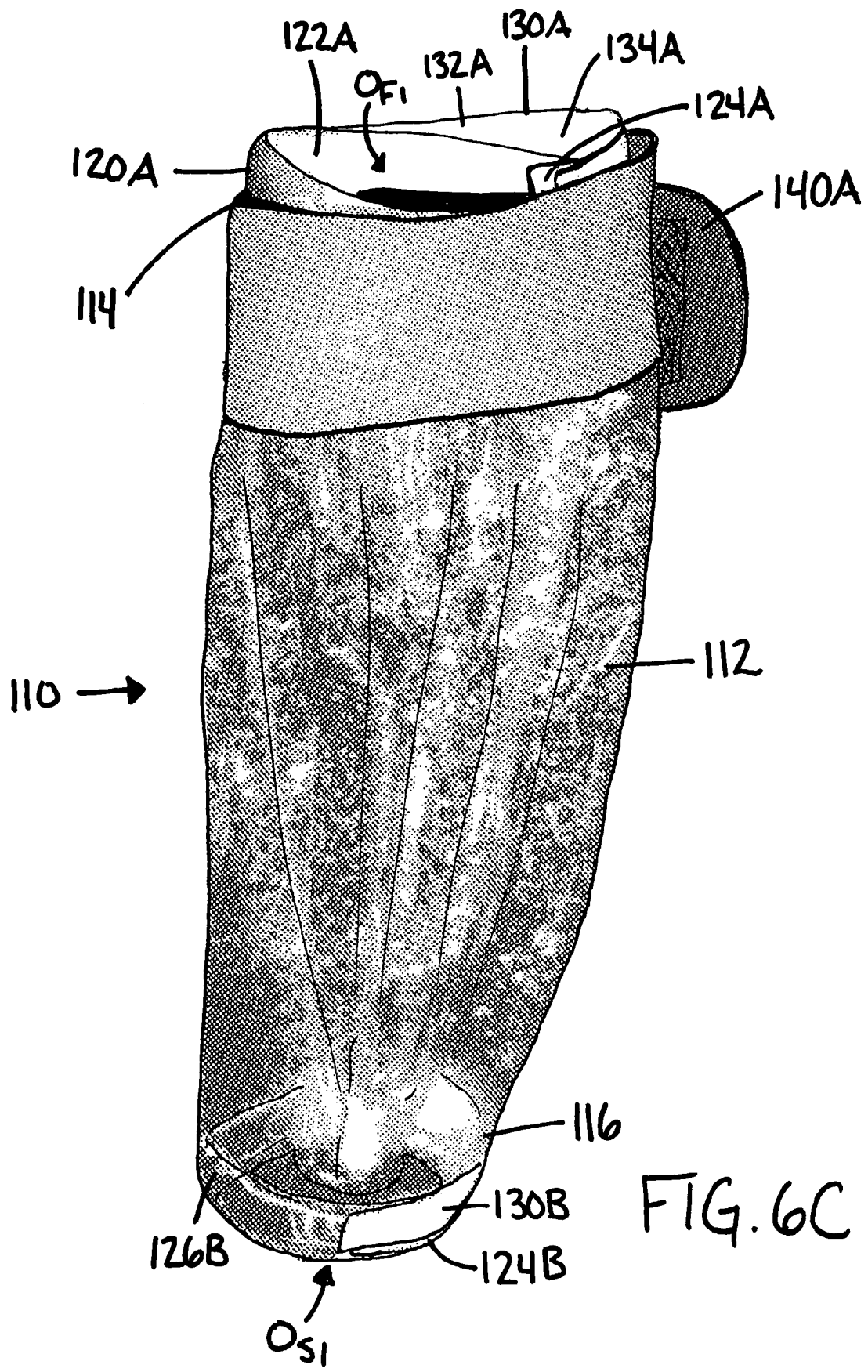

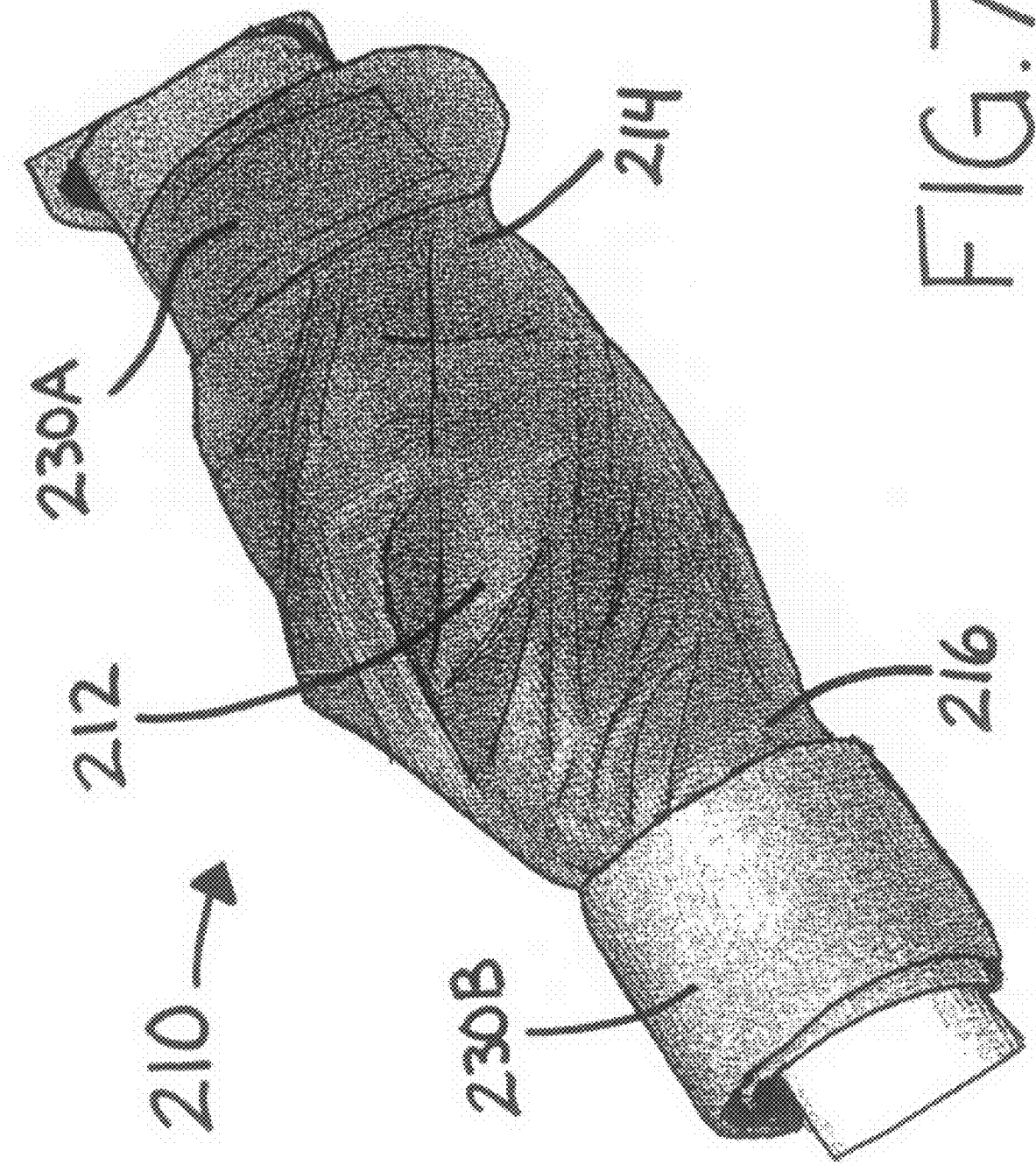

ADJUSTABLE IV CATHETER COVER DEVICE

RELATED APPLICATIONS

The presently disclosed subject matter claims the benefit of U.S. Provisional Patent Application Ser. No. 60/838,259, filed Aug. 17, 2006; the disclosure of which is incorporated herein by reference in its entirety.

TECHNICAL FIELD

The subject matter disclosed herein relates generally to an IV catheter cover device. More particularly, the subject matter disclosed herein relates to an adjustable catheter cover device that utilizes a single motion enclosure structure at each end of the sleeve.

BACKGROUND

IV catheter cover sleeves have been available in the past that provide protection and a degree of modesty for children with indwelling catheters. The machine washable fabric sleeves have two Velcro closure tabs along the open length of the sleeve that can be used to close the sleeve on the inside of the arm. Such IV catheter cover sleeves have proven to be advantageous in providing protection as well as a degree of modesty for a person having an indwelling IV located in their arm. In addition to modesty, the device protects the user from events such as catching the cap of the IV on a doorknob or the like. However, these sleeves can be hard to adjust when both hands cannot be used.

Therefore, a need exists for an IV catheter cover that employs easy to use securement configurations to permit single motion closure of the IV catheter cover.

SUMMARY

In accordance with this disclosure, IV catheter cover devices are provided. It is, therefore, an object of the present disclosure to provide novel IV catheter cover devices that provide easy securement of the catheter cover device through a single motion enclosure structure. This and other objects as may become apparent from the present disclosure are achieved, at least in whole or in part, by the subject matter described herein.

The IV catheter cover device can be a fabric sleeve that utilizes a single motion enclosure structure at each end of the sleeve. The single motion closure system comprises an extended fastening tab attached to the cuff end of the sleeve which is intended to be used to pull the open end tight around the arm and then laid over a mating fastening portion attached at a spaced apart location also at the cuff end of the sleeve. The other cuff end of the fabric sleeve has an identical fastening tab attached for pulling the end snuggly closed and then securing the fastening tab to the mating fastening portion secured at a spaced apart location also at the other cuff end of the sleeve. The sleeve can be open along its length and adapted to be secured closed by three mating fastening devices.

It is an object of the presently disclosed subject matter to provide an adjustable IV catheter cover device.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which:

FIG. 1A illustrates a top perspective view of an embodiment of an IV catheter cover device according to the present subject matter before closure of the ends of the catheter cover device;

FIGS. 4A and 4B illustrate side views of embodiments of cuffs that can be used in the embodiment of the IV catheter cover device according to FIG. 1;

FIG. 5 illustrates a perspective view of the embodiment of the IV catheter cover device according to FIG. 1 in use on a patient's arm;

FIG. 6C illustrates a top perspective view of another embodiment of an IV catheter cover device according to FIG. 6A after closure of the ends of the catheter cover device and wrapping of a waterproof band about the ends of the catheter cover device; and FIG. 7 illustrates a perspective view of the embodiment of the IV catheter cover device according to FIGS. 6A, 6B, and 6C in use on a patient's arm.

DETAILED DESCRIPTION

Reference will now be made in detail to the description of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Figure 1B:
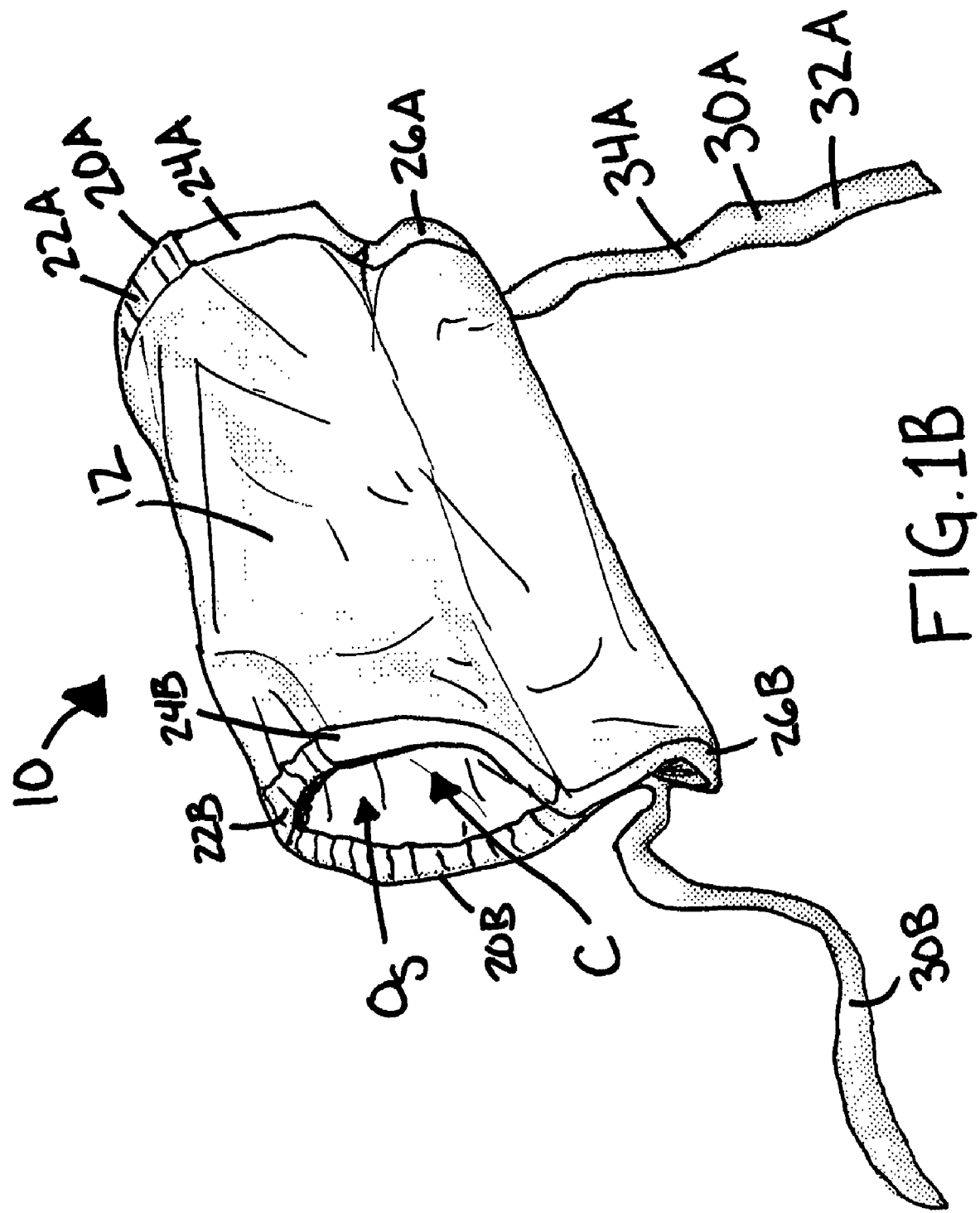
FIG. 1B illustrates a bottom perspective view of the embodiment of the IV catheter cover device according to FIG. 1 before closure of the ends of the catheter cover device.

FIGS. 1A and 1B illustrated an adjustable IV catheter cover device, generally designated as 10. Catheter cover device 10 can included a sleeve 12 which has a first end 14 and second end 16. Sleeve 12 can define a cavity C therein which passes through first end 14 and second end 16 of sleeve 12. Sleeve 12 can further define an access opening 18 which provides access into cavity C within sleeve 12. In use, a wearer of the adjustable catheter cover device 10 places sleeve 12 over the extremity by inserting the extremity through first end 14 and second end 16 of sleeve 12 such that a catheter which has been located in the extremity will be aligned with access opening 18. In this manner, sleeve 12 provides protection to the area in which the catheter is inserted into the extremity while providing cover to the catheter and, at the same time, providing easy access through access opening 18 defined within sleeve 12.

The catheter cover device 10 can also include a first cuff 20A and a second cuff 20B. The first cuff 20A can be integral to sleeve 12 at first end 14. First cuff 20A defines a first opening $O_F$ that leads into cavity C within sleeve 12. First cuff 20A has an elastic portion 22A, a fastening portion 24A disposed adjacent elastic portion 22A of the first cuff 20A, and a folding portion 26A between elastic portion 22A and fastening portion 24A of first cuff 20A.

Similarly, second cuff 20B which can be integral to sleeve 12 at the second end 16 defines a second opening $O_S$ (See FIG. 1B), which leads into cavity C. Second cuff 20B has a elastic portion 22B, a fastening portion 24B (See FIG. 1B) dispose adjacent elastic portion 22B of second cuff 20B and folding portion 26B disposed between the elastic portion 22B and fastening portion 24B of second cuff 20B. Sleeve 12 can be constructed so that both first and second cuffs 20A, 20B have a continuous circumference.

A first fastening tab 30A can be secured to first cuff 20A between elastic portion 22A and folding portion 26A of first cuff 20A. Similarly, a second fastening tab 30B can be is secured to second cuff 20B between elastic portion 22B and folding portion 26B of second cuff 20B. First fastening tab 30A and second fastening tab 30B can be configured to be engagable with the respective fastening portions 24A, 24B of first and second cuffs 20A, 20B to permit the respective first and second openings $O_F$, $O_S$ to be adjustable in size. In this matter, the openings $O_F$, $O_S$ and thus the cuffs 20A, 20B can be adjusted so that the catheter cover device 10 fits the associated extremity having a catheter therein on which catheter device 10 is placed.

In such a design, catheter cover device 10 can be secured to the extremity on which it is placed by closing first opening $O_F$ and second opening $O_S$ of first and second cuffs 20A, 20B to fit around the extremity on which it is placed. Thereby, sleeve 12 can be held in place to provide a protective cover around the catheter and the portion of the extremity on which it is placed. Further, each end 14, 16 of sleeve 12, and more particularly, cuffs 20A, 20B can be adjusted to such a closed position in a single motion.

This single motion closure is accomplished through the different portions of the cuffs 20A, 20B and the fastening tabs 30A, 30B. The fastening portions 24A, 24B of first and second cuffs 20A, 20B can include fastening devices which interact with fastening devices disposed on fastening tabs 30A, 30B, respectively, when a user closes the respective first and second openings $O_F$, $O_S$. These fastening devices can be any devices which can secure the fastening tabs 30A, 30B to the fastening portions 24A, 24B of the first and second cuffs 20A, 20B, respectively. For example, the fastening portions 24A, 24B may be a series of aligned male or female portions of snap buttons, while fastenings tabs 30A, 30B may have the matching portion of the snaps disposed along its length in alignment. Hook and loop fasteners as shown in FIGS. 1A and 1B may also be used as fastening devices to secure fastening tabs 30A, 30B to fastening portions 24A, 24B. For example, the fastening portions 24A, 24B of first and second cuffs 20A, 20B can be either the loop portion or the hook portion of a hook and loop fastener with the other matching portion disposed on the respective first and second fastener tabs 30A, 30B.

For example, fastening portions 24A, 24B of first and second cuffs 20A, 20B may extend over a specified length of each respective cuff 20A, 20B. The portion of the hook and loop fastener that comprises the fastener portions 24A, 24B can extend over this length. Similarly, fastening tabs 30A, 30B may have front and back sides with the front side being defined as the side of fastening tabs 30A, 30B which contain the other portion of the hook and loop fastener which interacts with the respective matching portion on fastening portions 24A, 24B. For each cuff 20A, 20B, the corresponding folding portion 26A, 26B is positioned between fastening portions 24A, 24B and the respective portion of each cuff 20A, 20B to which the respective fastening tab 30A, 30B is secured. Sides 32A, 32B of the respective fastening tabs 30A, 30B which face the respective cuffs 20A, 20B when wrapped therearound have respective fastening sections 34A, 34B as described above which can engage with the fastening portion 24A, 24B of the respective cuffs 20A, 20B to allow for the adjustability of the first and second openings $O_F$, $O_S$.

In this manner, when each fastening tab 30A, 30B is pulled and wrapped around the respective cuff 20A, 20B, its corresponding fastening section 34A, 34B on respective side 32A, 32B engages the fastening portion 24A, 24B of the respective cuff 20A, 20B. As the respective fastening tabs 30A, 30B are pulled towards fastening portion 24A, 24B of the cuffs 20A, 20B, each folding portion 26A, 26B is bunched together or folds upon itself to effectively decrease the size of respective opening $O_F$, $O_S$. By not having elastic within folding portions 26A, 26B, the folding portions 26A, 26B more readily permit secure and comfortable closing of the openings $O_F$, $O_S$ around the patient's arm when the fastening tabs 30A, 30B are secured to the fastening portions 24A, 24B. By providing the folding portions 26A, 26B between tabs 30A, 30B and fastening portions 24A, 24B, a wider range of adjustability for the openings $O_F$, $O_S$ can be obtained while maintaining maximum comfortable for the patient wearing the catheter cover device.

The elastic portions 22A, 22B of the cuffs 20A, 20B can be provided between the portion where fastening tabs 30A, 30B are secured to the cuffs 20A, 20B and fastening portions 24A, 24B of the cuffs 20A, 20B. Elastic portions 22A, 22B allows added stretch to cuffs 20A, 20B over a selected portion of the cuffs 20A, 20B without requiring such elastic portions to extending around the full cuffs 20A, 20B. Elastic portions 22A, 22B permit stretching of cuff 20A, 20B when fastening tabs 30A, 30B are being wrapped in a single motion into or out of engagement with fastening portions 24A, 24B. This stretch allows for a snug but comfortable fit around the extremity of the patient on which the openings $O_F$, $O_S$ are adjusted to fit. At the same time, by having the elastic portions 22A, 22B only extending partially around cuffs 20A, 20B and not between the fastenings portions 24A, 24B and the fastening tabs 30A, 30B in the direction in which fastening tabs 30A, 30B are wrapped towards fastening portions 24A, 24B, the elastic portions 22A, 22B cannot hinder the adjusting of the openings $O_F$, $O_S$ or create discomfort for the wearer when the fastening tabs 30A, 30B are secured to the fastening portions 24A, 24B of the cuffs 20A, 20B.

The elastic portions 22A, 22B also aid in holding the catheter cover device 10 in place upon the extremity of the patient before the fastening tabs 30A, 30B are fastened to fastening portions 24A, 24B of cuffs 20A, 20B. The elastic portions helped draw that portion of the respective cuffs 20A, 20B around the patient's extremity on which it is placed creating a friction which helps to loosely hold the catheter cover device 10 in place upon the extremity.

Elastic portions 22A, 22B can be created by inserting an elastic member such as an elastic band, within the cuff along the portion of the sleeve which creates the elastic portions 22A, 22B. The elastic member can be stretched to its extended length and then attached to the portion of the sleeve or fabric which creates the cuff. When the elastic member relaxes, it creates the respective elastic portion 22A, 22B.

As described above, the sleeve 12 can define an access opening 18 in a position between the first end 14 and the second end 16 of the sleeve 12. The access opening can extend from one cuff 20A to the second cuff 20B or at any portion therealong such that the access opening has a length that extends in a direction transverse to the first and second cuffs 20A, 20B. Sleeve 12 can further include a first border 36A and a second border 36B which defined the access opening 18. The first and second borders 36A, 36B can be configured to overlap to permit closure of access opening 18. In such a manner, first border 36A can be an outer border which overlaps the second border 36B that serves as an inner border when the access opening 18 is closed. Fastening devices 38 may be secured along the first and second borders 36A, 36B such that the fastening devices 38 of second border 36B interact with the fastening devices of first border 36A when first border 36A overlaps second border 36B. For example, the fastening devices 38 can be hook-and-loop fasteners with the hook portion being secured to one of the first or second borders 36A, 36B and the loop portion being secured to the other of the first and second borders 36A, 36B. The hook-and-loop portions can be aligned so that they attach to one another when first and second borders 36A, 36B overlap one another. The first and second borders 36A, 36B are securable in a closed position even when at least one of the first and second openings $O_F$, $O_S$ is fully extended with elastic portions 22A, 22B fully stretched.

Figure 2A:
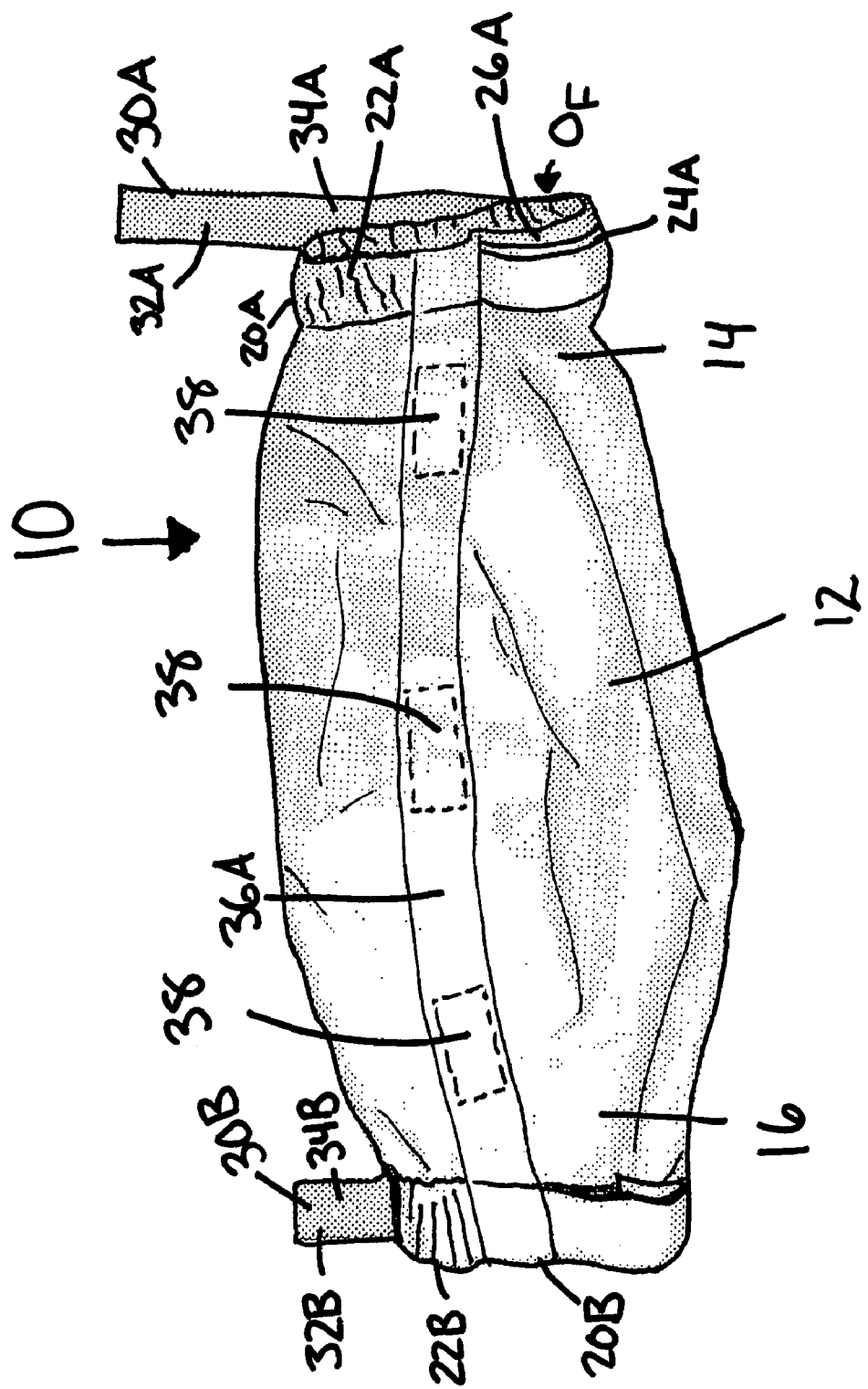
FIG. 2A illustrates a top perspective view of the embodiment of the IV catheter cover device according to FIG. 1 after closure of the ends of the catheter cover device.
Figure 2B:
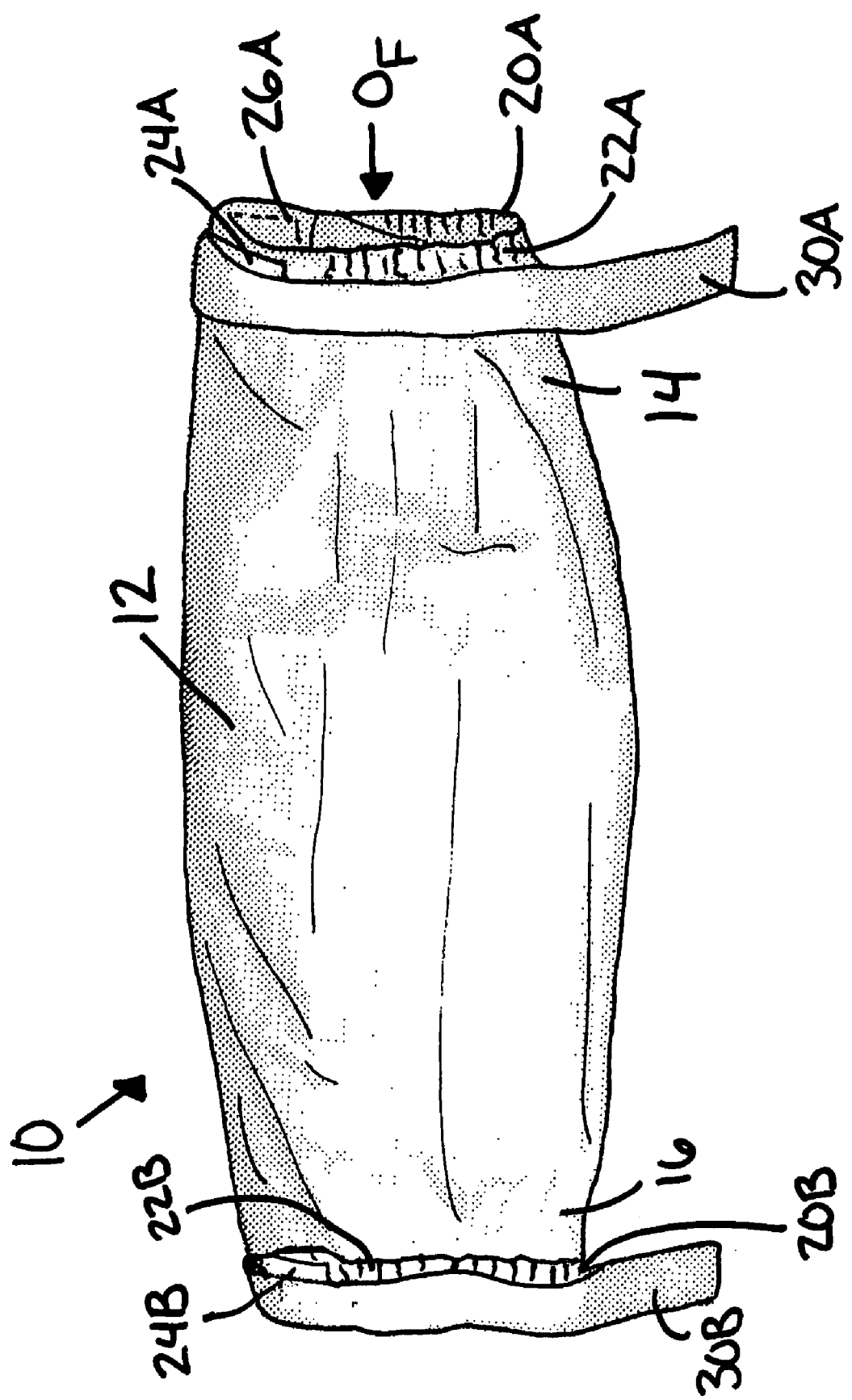
FIG. 2B illustrates a bottom perspective view of the embodiment of the IV catheter cover device according to FIG. 1 after closure of the ends of the catheter cover device.

FIGS. 2A and 2B show catheter cover device 10 with cuffs 20A, 20B and first and second openings $O_F$, $O_S$ adjusted to a restricted size by having first and second tabs 30A, 30B wrapped around cuffs 20A, 20B such that fastening sections 34A, 34B on sides 32A, 32B are secured to fastening portions 24A, 24B of first and second cuffs 20A, 20B. Further, first and second borders 36A, 36B of sleeve 12 are in a closed position such that fastening devices 38 of the first and second borders 36A, 36B are fastened together. First fastening tab 30A has been pulled and wrapped around cuff 20A in a single motion such that folding portion 26A of cuff 20A folds upon itself. The fastening portion 34A of fastening tab 30A engages the fastening portion 24A of cuff 20A to hold cuff 20A and first opening $O_F$ in this restricted position. In this manner, once the patient has placed the catheter cover device 10 onto the extremity in which the indwelling IV catheter has been placed, catheter cover device 10 is position such that sleeve 12 covers the catheter with the access opening 18 aligned to allow access to the catheter as needed. At this point, cuff 20A can be closed around the extremity of the patient to hold it in place to help protect the catheter and patient.

Cuff 20B can be adjusted in a similar manner. Fastening tab 30B attached to second cuff 20B can be pulled and wrapped around second cuff 20B in a single motion until fastening portion 34B on side 32B engages fastening portion 24B of second cuff 20B. By pulling fastening tab 30B and wrapping it around cuff 20B to fasten it against fastening portion 24B of second cuff 20B, folding portion 26B folds upon itself, thereby adjusting second cuff 20B to a restricted position and decreasing the size of second opening $O_S$ (See FIG. 1B). In this manner, the second opening $O_S$ and second cuff 20B can be adjusted to the appropriate size to fit the extremity on which the catheter cover 10 has been placed to secure the second end 16 of sleeve 12 to the extremity of the patient on which catheter cover 10 is placed.

Once catheter cover device 10 is properly placed on the extremity of the patient such that sleeve 12 covers the catheter and access opening 18 is aligned therewith, first and second cuffs 20A, 20B can be adjusted in the manner described above so that openings $O_F$, $O_S$ and first and second cuffs 20A and 20B fit the portions of the extremity of the patient on which they are placed. Elastic portions 22A and 22B of first and second cuffs 20A, 20B allow flexibility in such securement and allow for different levels of tightness with which the first and second cuffs 20A, 20B fit around the extremities.

As mentioned above, in some embodiments, sleeve 12 may not define an access opening therein so that the sleeve covers the catheter and will be removed when it is time for the catheter to be used.

Figure 3C:
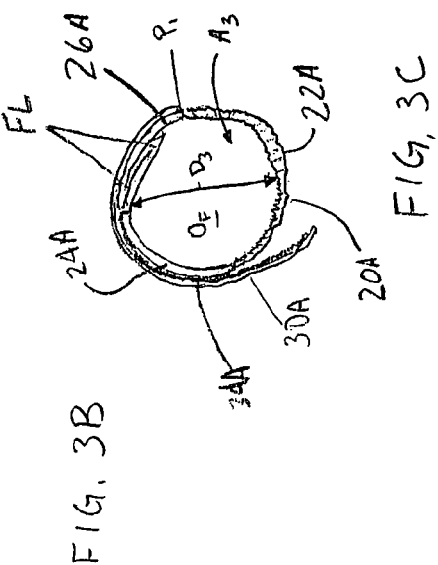
FIG. 3C illustrates a side end view of the embodiment of the IV catheter cover device according to FIG. 1 after closure of the ends of the catheter cover device.
Figure 3B:
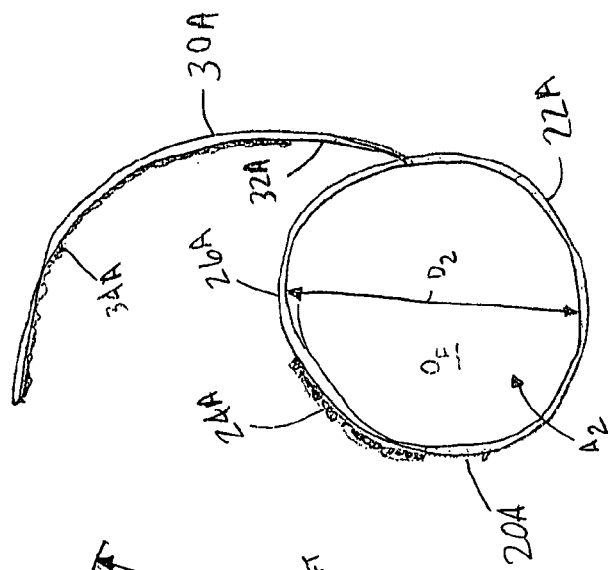
FIG. 3B illustrates a side end view of the embodiment of the IV catheter cover device according to FIG. 1 that is extended and before closure of the ends of the catheter cover device.
Figure 3A:
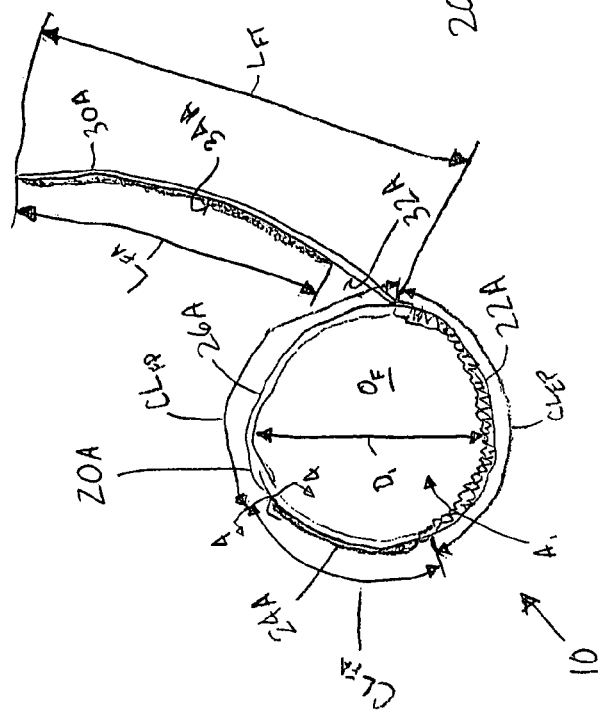
FIG. 3A illustrates a side end view of the embodiment of the IV catheter cover device according to FIG. 1 that is not extended and before closure of the ends of the catheter cover device.

FIGS. 3A, 3B and 3C illustrate an end view of first cuff 20A in different positions that it can assume during use. As shown in FIG. 3A, cuff 20A is held in its resting position with opening $O_F$ in a circular shape. Normally, first cuff 20A is made up of materials which are not rigid such as plastics or fabrics and would thus not normally take on such a symmetrical shape unless placed around something having that shape. Thus, opening $O_F$ and first cuff 20A are permitted to take on the shape of the object around which they are placed. Often, opening $O_F$ takes on an irregular shape based on the extremity on which it is placed or, when not in use, such a shape is shown in FIGS. 1A and 1B. For the purpose of illustration, FIGS. 3A, 3B and 3C show cuff 20A and thus opening $O_F$, in the symmetrical circular shape.

Cuff 20A is in a semi-relaxed state with elastic portion 22A unexpanded as shown in FIG. 3A. First cuff 20A has a first circumferential length as measured around the circumference of the outer portion of the cuff 20A. Similarly, the second cuff will also have a circumferential length. Such circumferential lengths are measured when elastic portions 20A, 20B are unexpanded. These circumferential lengths may vary or can be equal to one another in length.

Figure 4A:
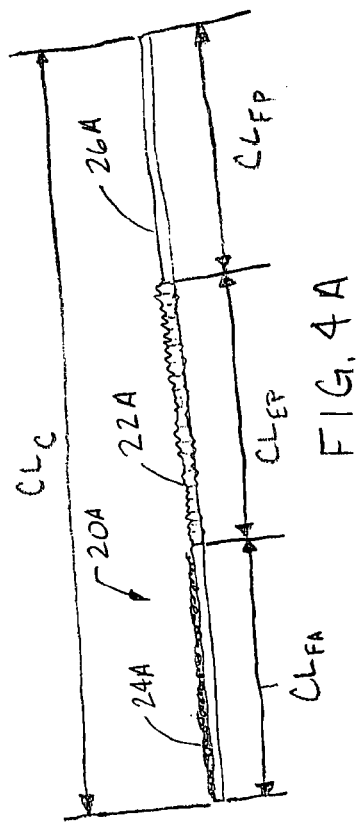

The circumferential length is more accurately illustrated in FIG. 4A. First cuff 20A has a circumferential length $CL_C$, while each portion has it own length. As shown in FIG. 4A, fastening portion 24A has a length $CL_{FA}$, while elastic portion 22A has a length $CL_{EP}$ and folding portion 26A has a length $CL_{FP}$. Elastic portion 22A may comprise about one-third of circumferential length $CL_C$ of first cuff 20A. Thus, length $CL_{EP}$ of elastic portion 22A may comprise about one-third of circumferential length $CL_C$. Similarly, each portion 22A, 24A, 26A of first cuff 20A may comprise about equal lengths.

In such a design, enough material is provided to allow for proper folding and creasing of the folding portion 26A when fastening tab 30A is pulled towards fastening portion 24A of cuff 20A. Further, fastening portion 24A has enough material to allow a wider range of adjustment of opening $O_F$ and cuff 20A.

In FIG. 3A, opening $O_F$ defined by first cuff 20A has a diameter $D_1$ when elastic portion 22A is unexpanded. Thus, in this semi-relaxed position, opening $O_F$ has an area $A_1$.

Similarly, fastening tab 30A has a length $L_{FT}$ which is long enough to provide a surface on which fastening portion 34A can be secured to allow for a wide range of adjustability of cuff 20A. For example, fastening tab 30A may have a length $L_{FT}$ that is about two-thirds of circumferential length $CL_C$ of cuff 20A. In such an embodiment, length $L_{FT}$ of fastening tab 30A can extend around an unfolded folding portion 26A and fully cover fastening portion 24A of cuff 20A. Further, the fastening section 34A attached to side 32A of fastening tab 30A may have length $L_{FA}$. Length $L_{FA}$ can be equal to the length $L_{FT}$ of the fastening tab 30A. Alternatively, length $L_{FA}$ for fastening portion 34A can be less than total length $L_{FT}$ of fastening tab 30A as shown in FIGS. 3A-3C. However, the longer the length $L_{FA}$ of fastening portion 30A, the wider the range for adjustability of cuff 20A.

FIG. 3B shows cuff 20A in an extended position such that elastic portion 22A is fully stretched. In such a manner, opening $O_F$ is at its largest with a diameter $D_2$ and an area $A_2$. Thereby, diameter $D_2$ is greater in distance than diameter $D_1$ and thus, the area of opening $O_F$ is enlarged from area $A_1$ to the larger area $A_2$. This represents the maximum size of the extremity on which catheter cover device 10 may be placed. In such embodiments, the circumferential length of cuff 20A is thus increased as the elastic portion 20A is fully stretched. The diameter of the cross-section of the sleeve 12 as shown in FIG. 1A can be greater than diameter $D_2$ of opening $O_F$ such that even in the fully stretched position of elastic member 22A, catheter cover device 10 can still be used while still giving room to comfortably cover the catheter placed within the extremity. Normally, however, a different sized catheter cover with larger cuffs 20A which allow for a larger diameter for opening $O_F$ will be used on extremities which would fully extend elastic portion 20A to allow for greater comfort for the wearer. Still, the elasticity of elastic portion 22A provides for such fully extended use if needed. In such an embodiment, fastening tab 30A may still be placed around cuff 20A such that fastening section 34A of fastening tabs 30A will engage fastening portion 24A of cuff 20A without restricting the size of opening $O_F$ and therefore cuff 20A.

FIG. 3C illustrates cuff 20A where the first cuff 20A and the first opening $O_F$ have been adjusted to a restricted size by a single motion of pulling and wrapping fastening tab 30A around cuff 20A such that folding portion 26A folds upon itself creating folds $F_L$. By pulling and wrapping fastening tab 30A in this manner, the size of cuff 20A is decreased from its unwrapped unexpanded diameter of $D_1$ to this wrapped diameter of $D_3$. Consequently, catheter cover device 10 may be placed on an extremity with cuff 20A in its unexpanded and unwrapped position as shown in FIG. 3A.

Elastic portion 22A can help to hold the catheter cover device 10 on the extremity on which it is placed even if the extremity does not occupy the full area $A_1$ of opening $O_F$. Fastening tab 30A may then be wrapped around cuff 20A to adjust cuff 20A and the opening $O_F$ to restrict cuff 20A and opening $O_F$ to fit around the extremity which occupies the cross-sectional area $A_3$.

Folding portion 26A extends between position $P_1$ where fastening tab 30A attaches to cuff 20A and the fastening portion 24B. Folding portion 26A allows for a smooth fit around the extremity to permit a comfortable and adequate closing around the extremity by permitting smooth folds $F_L$, or creases, of the material of cuff 20A at folding portion 26A. Elastic members or fastening members occupying folding portion 26A would inhibit such comfortable and smooth folding by stiffening folding portion 26A. Thus, folding portion 26A has increased flexibility over elastic portions 22A and fastening portions 24A. This decreased rigidity that resides in folding portion 26A permits a better fit as well as a more comfortable fit when cuff 20A is secured around the extremity of the patient. Further, by having elastic portion 22A on the outside of where fastening tab 30A wraps around cuff 20A, elastic portion 22A provides added comfort by allowing a certain amount of stretch once fastening tab 30A is pulled and wrapped around and engaged with fastening portion 24A while not creating a constriction around the extremity on which cuff 20A is placed.

FIG. 4B shows a further embodiment of a cuff 20A' which has been dissected and stretched to illustrate the circumferential length of cuff 20A'. As shown in FIG. 4B, 20A' has a circumferential length $CL_C$. However, the elastic portion 22A' has a larger circumferential length $CL_{EP1}$ than that of the cuff 20A shown in FIG. 4A. Thus, elastic portion 22A' is larger in length than fastening portions 24A' and folding portion 26A'. Further, length $CL_{EP1}$ of elastic portion 22A' is larger than the length $CL_{FA1}$ of the fastening portion 24A' and length $C_{FP1}$ of folding portion 26A'. For example, length $CL_{EP1}$ of elastic portion 22A' may be about one-half of the length $CL_C$ of the cuff 20A'. Such an embodiment allows for more stretch while still permitting the tight closure by providing folding portion 26A' when the cuff 20A' of the associated catheter cover device 10 is placed on an extremity of a patient.

FIG. 5 illustrates a catheter cover device 10 placed upon an arm E of a patient to allow coverage of catheter CT placed within arm E. As stated above, arm E can be placed through first opening $O_F$ formed by cuff 20A and then second opening $O_S$ formed by cuff 20B to allow placement of catheter cover device 10 where sleeve 12 can cover catheter CT while still providing an access opening 18 within sleeve 12 to access catheter CT as needed. The fastening tab 30A can be wrapped around cuff 20A as described above to adjust opening $O_F$ and cuff 20A to securely fit around arm E on an upper portion U of the arm E so that the fastening tab 30A is secured to the fastening portion of first cuff 20A. Similarly, fastening tab 30B may be pulled and wrapped in a single motion around cuff 20B so as to adjust cuff 20B and opening $O_S$ to securely fit around a lower portion L of arm E. The catheter cover device 10 will be held in place to allow the patient to be active without fear of catheter cover device 10 slipping off. Thereby, catheter cover device 10 protects the arm E where the catheter CT is placed. As can be seen from FIG. 5, first cuff 20A and opening $O_F$ are independently adjustable to different sizes from second cuff 20B and opening $O_S$ to permit individualized fits at different locations on the arm E.

As shown in FIG. 5, sleeve 12 may include first border 36A and second border 36B which defined access opening 18. First border 36A overlaps second border 36B to permit closure of access opening 18. First and second borders 36A, 36B can further include fastening devices 38 which interact with one another to secure first border 36A to second border 36B for a secure closure of access opening 18. Such a design permits easy access through sleeve 12 to catheter CT and arm E while still permitting protection of both arm E and catheter CT when access opening 18 is closed.

Figure 6A:
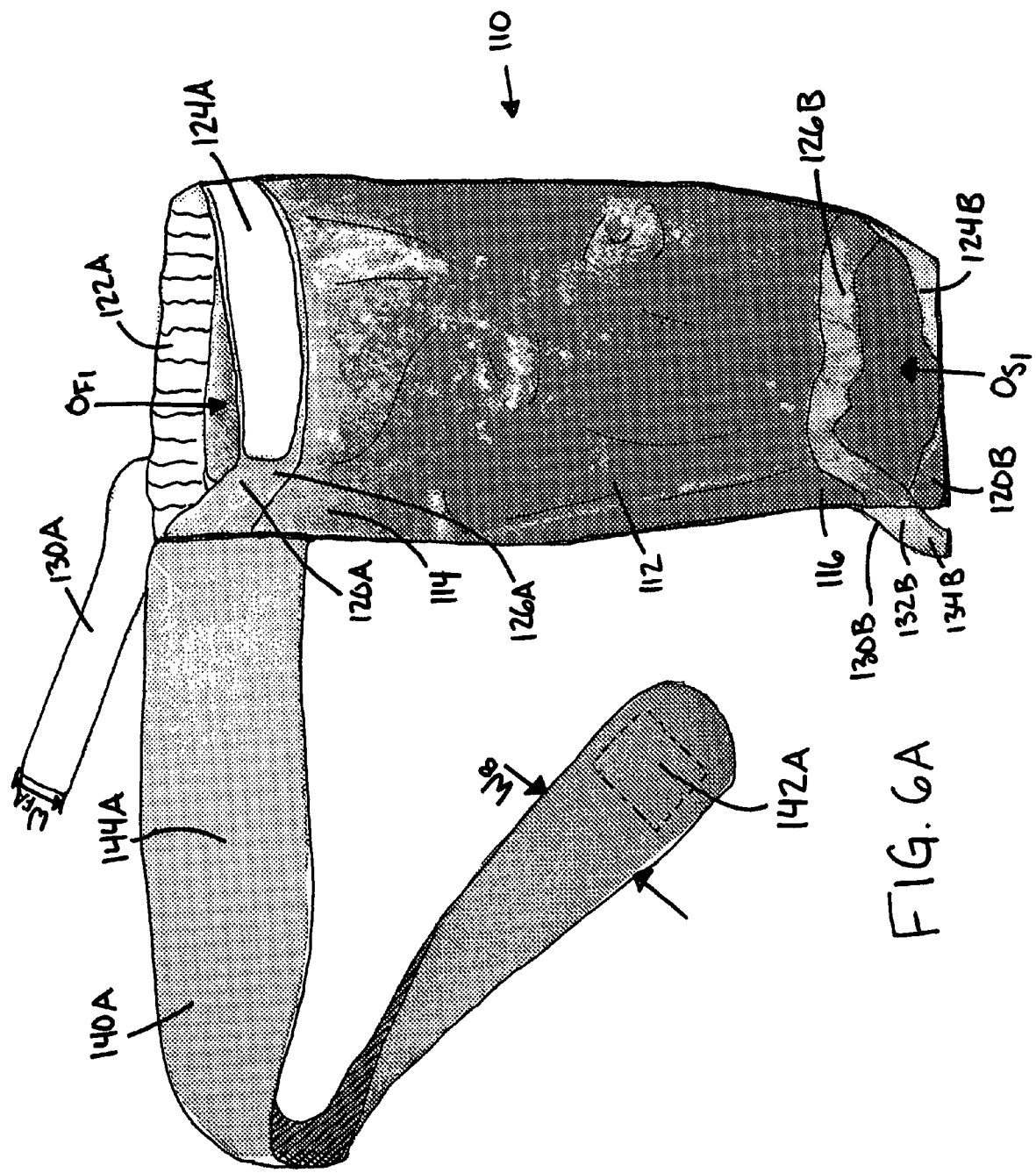
FIG. 6A illustrates a top perspective view of another embodiment of an IV catheter cover device according to the present subject matter before closure of the ends of the catheter cover device.

FIGS. 6A-7 illustrate another embodiment of a catheter cover device that can provide a waterproof barrier around a catheter residing in an extremity of a user. In particular, a catheter cover device, generally designated as 110, is provided with a sleeve 112 having a first end 114 and a second end 116. Sleeve 112 is constructed from a water repellent material. For example, sleeve 112 can be constructed of a plastic seamless material which defines a cavity inside of the sleeve 112. The catheter device 110 may also include a first cuff 120A integrally disposed to sleeve 112 on first end 114 and a second cuff 120B integrally disposed to sleeve 112 on the second end 116. Sleeve 112 can be constructed so that both first and second cuffs 120A, 120B have a continuous circumference. As described above, first cuff 120A can include an elastic portion 122A, fastening portion 124A disposed beside of elastic portion 122A and a folding portion 126A disposed between elastic portion 122A and fastening portion 124A. First cuff 120A defines an opening $O_{F1}$ which leads into the cavity formed by sleeve 112.

A fastening tab 130A can be attached to cuff 120A between elastic portion 122A and folding portion 126A such that fastening tab 130A can be wrapped around first cuff 120A in a single motion to adjust the size of first cuff 120A and opening $O_{F1}$. As described above, fastening tab 130A can have a fastening section 134A disposed on side 132A which faces cuff 120A when fastening tab 130A is wrapped therearound. Fastening section 134A of fastening tab 130A engages the fastening portion 124A of first cuff 120A to create a secure engagement which holds first cuff 120A and opening $O_{F1}$ in its adjusted position.

Similarly, second cuff 120B can include an elastic portion 122B and a fastening portion 124B disposed beside the elastic portion 122B with a folding portion 126B disposed between the other sides of elastic portion 122B and folding portion 126B. Second cuff 120B forms an opening $O_{S1}$ leading into the cavity formed by sleeve 112. A second fastening tab 130B can be secured to cuff 120B between elastic portion 122A and folding portion 124A.

Second fastening tab 130B includes a fastening section 134B on side 132B which faces second cuff 120B when second fastening tab 130B is wrapped therearound. Second fastening tab 130B can be pulled and wrapped around second cuff 120B such that fastening portion 134B engages the fastening portion 124B to adjust the size of cuff 120B and opening $O_{S1}$ and hold the cuff 120B in this adjusted position. Preferably, in most embodiments, the fastening tabs 130A, 130B can be wrapped around the folding portions 126A, 126B of the respective cuffs 120A, 120B so that that the folding portions 126A, 126B fold upon themselves as described in detail above.

Such a catheter cover device 110 permits the user to cover the catheter in the patient's extremity and prevent water from entering therethrough by using the waterproof plastic material to cover the portion of the extremity in which the catheter is placed. Thereby, the catheter is kept dry.

To further enhance this proofing ability of the catheter cover device 110, a first waterproof band 140A can be secured to at least one of the first cuff 120A or sleeve 112. Waterproof band 140A can have a width $W_B$ which is larger than the width $W_{FA}$ of the fastening tab 130A as well as the width of first cuff 120A. Further, first waterproof band 140A can have a length which is longer than the length of fastening tab 130A. In this manner, first waterproof band 140A can be wrapped around the adjusted cuff 120A to cover the first end 114 of sleeve 112 after first fastening tab 130A has been used to adjust the first opening of $O_{F1}$ to fit a patient's extremity on which sleeve 112 has been placed.

Waterproof band 140A has a length which permits a total wrapping around of first cuff 120A to thereby provide a seal to prevent entry of water through the opening $O_{F1}$ at the first end 114 of sleeve 112. First waterproof band 140A can include a fastening device 142A disposed thereon which can interact with a side 144A of first waterproof band 140A. In this manner, after wrapping first waterproof band 140A around the adjusted first cuff 120A at least one time, the fastening device 142A can engage a portion of side 144A of the first waterproof band 140A to secure waterproof closure of opening $O_{F1}$ and first cuff 120A around the extremity of the patient. For example, fastening device 142A can be a hook fastener that can be secured to the first waterproof band 140A. Alternatively, matching fastening devices can be attached to either side of the waterproof band to permit securement of the waterproof band around the cuff of the sleeve and the extremity. For example, the matching fastening devices can comprise hook and loop fasteners, a plurality of snaps, a plurality of magnets, etc. First waterproof band 140A can comprise a strip of neoprene. The length of first waterproof band 140A can be such that the waterproof band 140A wraps around a fully extended cuff 120A and opening $O_{F1}$ at least two times. However, the waterproof band 140A may be wrapped around cuff 120A between one and two times.

Figure 6B:
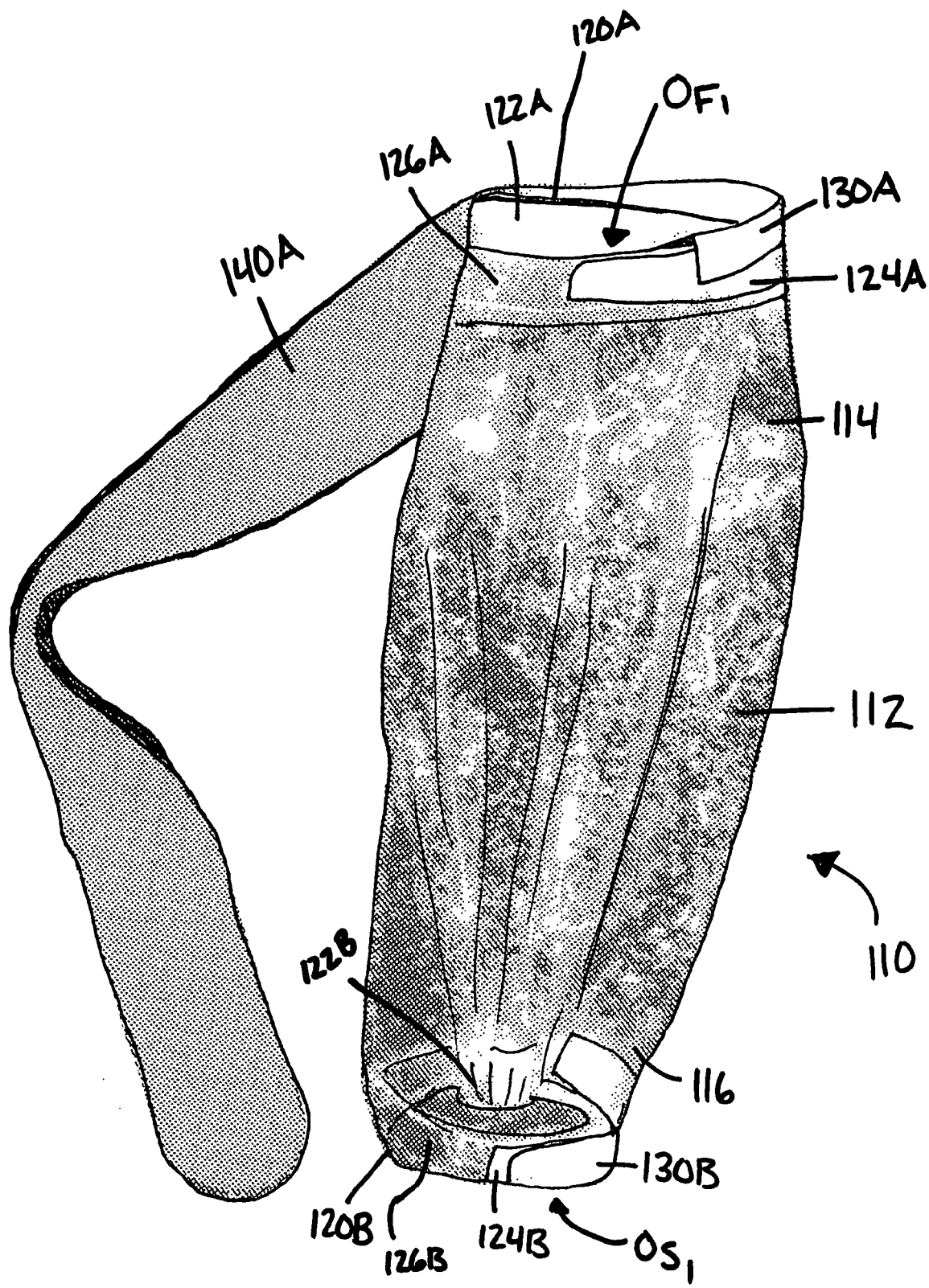
FIG. 6B illustrates a top perspective view of another embodiment of an IV catheter cover device according to FIG. 6A after closure of the ends of the catheter cover device.

In use, catheter cover device 110 may be placed onto an extremity of a patient having a catheter therein such that sleeve 112 covers the extremity as well as the catheter. Fastening tab 130A may be pulled and wrapped around cuff 120A in a single motion such that first cuff 120A and opening $O_{F1}$ are adjusted to a restricted position with folding portion 126A folding in upon itself. Similarly, second fastening tab 130B can be pulled and wrapped around second cuff 120B in a single motion such that the fastening portion 134B of fastening tab 130B engages fastening portion 124B of second cuff 120B so that second cuff 120B and second opening $O_{S1}$ are adjusted to a restricted position around the extremity on which it is placed to secure cuff 120B and sleeve 112 to the patient as shown in FIG. 6B.

At this point, first waterproof band 140A can then be wrapped around first cuff 120A at least two times to seal off opening $O_{F1}$ to prevent water from entering through opening $O_{F1}$. Thereby, the patient is allowed to take a bath or shower without fear of contaminating the catheter. In this manner, water will not drain down the extremity and in through opening $O_{F1}$ while sleeve 112 provides protective dry covering for the portion of the extremity in which the catheter is placed. In this manner, the catheter cover device 110 can be secured to the arm in a comfortable fashion by adjusting the cuffs 120A and 120B using fastening tabs 130A, 130B and fastening portions 124A and 124B of the cuffs 120A, 120B. The first opening $O_{F1}$ can then be made waterproof by wrapping the first waterproof band 140A around first cuff 120A to seal off opening $O_{F1}$ to further prevent any unwanted water from entering and contaminating the catheter which sleeve 112 is protecting.

Similar to the first waterproof band 140A, a second waterproof band (not shown) may be secured to at least one of the second cuff 120B or sleeve 112. The second waterproof band can have a larger width and length than the second fastening tab 130B to permit wrapping of the second waterproof band around the second cuff 120B after the second fastening tab 130B has been used to adjusted the second opening $O_{S1}$ to fit the patient's extremity on which the sleeve 112 has been placed. Thereby, the second waterproof band provides a waterproof seal to prevent entrance of water through the second opening $O_{S1}$ of the second end 116 of sleeve 112. Second waterproof band can also have a fastening device to hold the band in its wrapped position once it is wrapped around second cuff 120B. As with the first waterproof band 140A, the second waterproof band can also comprise a strip of neoprene which has a length that permits wrapping of the second waterproof band around a fully extended second opening $O_{S1}$ at least two times. Alternatively, the second waterproof band may be wrapped around cuff 120B between one and two times.

FIG. 7 illustrates a further embodiment in which a catheter cover device 210 is provided which can have a sleeve 212 that is made from a water repellant material. Sleeve 212 can have a first end 214 and second end 216. A first cuff can be disposed integrally to the sleeve 212 at first end 214 and a second cuff can be integrally disposed on sleeve 212 and second end 216. Both the first and second cuffs can be constructed as described above wherein each cuff comprises an elastic portion, a fastening portion, and folding portion with the folding portion disposed between the elastic portion and fastening portion. Fastening tab 230A may be secured to either the first cuff or the first end 214 of the sleeve 212, while a second waterproof fastening tab 230B may be secured to the second cuff and/or the second end 216 of the sleeve 212.

The waterproof fastening tabs 230A, 230B operate similar to both the waterproof bands and the fastening tabs described above. The waterproof fastening tabs may have a fastening section which interacts with the fastening portion of the respective cuff around which it wraps. Waterproof fastening tabs 230A, 230B can also have a further fastening device which allows each waterproof fastening tab 230A, 230B to secure to itself after wrapping multiple times around the extremity on which it is placed. Waterproof fastening tabs 230A, 230B thereby provide a waterproof seal around the cuffs to prevent water from leaking into the sleeve area and provide a dry environment for the catheter over which sleeve 212 is placed. In this manner, catheter cover device 210 can be secured by a single motion wrap of each waterproof fastening tab 230A, 230B with its fastening section interacting with the fastening portion of the respective cuff to secure the sleeve 212 and catheter cover device 210 to the extremity on which it is placed. Then, waterproof fastening tabs 230A, 230B can be continued to be wrapped around the cuff and the extremity to provide the waterproof seal at either end of the catheter device 210.

As shown in FIG. 7, in a device placed on the patient's arm, each cuff and respective waterproof fastening tab 230A, 230B can be independently adjusted to provide adequate waterproof seal to different areas of the extremity on which it is placed. In this manner, waterproof protection is provided to the catheter placed within the extremity of the patient as well as the area of the extremity on which the catheter is placed. Although the plastic sleeve can be made from many different types of flexible plastic or plastic type materials, it is presently believed that the sleeve can be made from GORETEX® or a similar material. The plastic sleeve can be seamless so as to improve the ability of the sleeve to prevent water from entering therein and perhaps cause a contamination hazard to the IV site that is being protected by the sleeve.

The catheter cover devices described above provide for a measure of protection and a degree of modesty for children and adults with indwelling catheters. The machine washable catheter cover device can close with hook and loop closure tabs on the wrist and just above the elbow and can feature elastic for a comfortable adjustable fit. There can be three closures along the length of the sleeve for breathability and protection against snags. The waterproof versions as described in FIGS. 6A, 6B, 6C, and 7 are lightweight and flexible as well as nonbinding. In this manner they fit loosely in order to reduce condensation caused by sweating of the portion of the extremity covered by the sleeve.

The catheter cover devices can come in different sizes for both children and adults. For example, children may have sizes in small, medium, and large, while adults may have the sizes of small, medium, large, and extra-large. For such catheter cover devices, the lengths may vary as well as the openings at either end created by the cuffs attached thereto. For example, the lengths for children's catheter covers can be, for example, four to six inches for a small catheter cover, seven to ten inches for a medium catheter cover, and ten to fourteen inches for a large catheter cover. For adults, the lengths of the catheter covers can be, for example, ten to fourteen inches for a small catheter cover, fourteen to eighteen inches for medium catheter cover, eighteen to twenty-two inches for a large catheter cover, and twenty-two to twenty-six inches for an extra-large catheter cover. The cover sleeves of the catheter cover devices can be customized with logos or signs or pattern fabrics to make them more fashionable for patients to wear.

Embodiments of the present disclosure shown in the drawings and described above are exemplary of numerous embodiments that can be made within the scope of the appending claims. It is contemplated that the configurations of the catheter cover device can comprise numerous configurations other than those specifically disclosed. The scope of a patent issuing from this disclosure will be defined by these appending claims.

What is claimed is:

1. An adjustable IV catheter cover device comprising:
   a sleeve defining a cavity therethrough, the sleeve having a first end and a second end;
   a first cuff integral to the sleeve at the first end and defining a first opening leading into the cavity, the first cuff having an elastic portion, a fastening portion disposed next to a first end of the elastic portion of the first cuff, and a folding portion disposed between the elastic portion and fastening portion of the first cuff;
   a first fastening tab secured to the first cuff at a second end of the elastic portion of the first cuff between the folding portion of the first cuff and the elastic portion of the first cuff, the first fastening tab configured to be engageable with the fastening portion of the first cuff to adjust the size of the first opening;
   a second cuff integral to the sleeve at the second end and defining a second opening leading into the cavity, the second cuff having an elastic portion, a fastening portion disposed next to an end of the elastic portion of the second cuff and a folding portion disposed between the elastic portion and fastening portion of the second cuff; and
   a second fastening tab secured to the second cuff at a second end of the elastic portion of the second cuff between the folding portion of the second cuff and the elastic portion of the second cuff, the second fastening tab configured to be engageable with the fastening portion of the second cuff to adjust the size of the second opening.

2. The catheter cover device according to claim 1, wherein the sleeve defines an access opening at a position between the first end and the second end.

3. The catheter cover device according to claim 2, wherein the access opening has a length that extends in a direction transverse to the first and second cuffs.

4. The catheter cover device according to claim 2, wherein the sleeve further comprises a first border and second border that defines the access opening, the first and second borders configured to permit overlapping to close the access opening.

5. The catheter cover device according to claim 4, further comprising fastening devices disposed on the first and second borders, the fastening devices configured to secure closure of the access opening.

6. The catheter cover device according to claim 4, wherein the first and second borders are securably closable when at least one of the first opening or second opening is fully extended.

7. The catheter cover device according to claim 1, wherein the sleeve comprises a protective fabric.

8. The catheter cover device according to claim 1, wherein the sleeve comprises a water repellant material.

9. The catheter cover device according to claim 8, wherein the sleeve is seamless.

10. The catheter cover device according to claim 8, wherein the water repellant material comprises a plastic.

11. The catheter cover device according to claim 8, further comprising a first waterproof band secured to at least one of the first cuff or the sleeve, the waterproof band having a larger width and length than the first tab to permit wrapping around the first end of the sleeve after the first tab has been used to adjust the first opening to an extremity on which the sleeve has been placed, thereby providing a seal to prevent entry of water through the first end of the sleeve.

12. The catheter cover device according to claim 11, further comprising a second waterproof band secured to at least one of the second cuff or the sleeve, the waterproof band having a larger width and length than the second tab to permit wrapping around the second end of the sleeve after the second tab has been used to adjust the second opening to an extremity on which the sleeve has been placed, thereby providing a seal to prevent entry of water through the second end of the sleeve.

13. The catheter cover device according to claim 12, wherein the first and second waterproof bands have fastening devices secured thereto to hold the bands in a wrapped position.

14. The catheter cover device according to claim 12, wherein the first and second waterproof bands comprise neoprene.

15. The catheter cover device according to claim 12, wherein the length of the first and second waterproof bands permits the wrapping the waterproof bands around a fully extended first or second opening, respectively, at least two times.

16. The catheter cover device according to claim 1, wherein the first cuff has a first circumferential length and the second cuff has a second circumferential length as measured when the elastic portions of the first and second cuffs are unexpanded.

17. The catheter cover device according to claim 16, wherein the elastic portion of the first cuff extends about one-third of the first circumferential length and the elastic portion of the second cuff extends about one-third of the second circumferential length.

18. The catheter cover device according to claim 17, wherein the first tab comprises a length of at least about two-thirds of the first circumferential length and the second tab comprises a length of at least about two-thirds of the second circumferential length.

19. The catheter cover device according to claim 16, wherein the elastic portion of the first cuff extends about one-half of the first circumferential length and the elastic portion of the second cuff extends about one-half of the second circumferential length.

20. The catheter cover device according to claim 19, wherein the first tab comprises a length of at least about one-half of the first circumferential length and the second tab comprises a length of at least about one-half of the second circumferential length.

21. The catheter cover device according to claim 1, wherein each of the fastening portions of the first and second cuffs comprise a hook portion or a loop portion of a hook and loop fastener and at least a section of each of the first and second fastening tabs comprise the other matching portion of the hook and loop fastener.

22. The catheter cover device according to claim 21, wherein the section comprising the matching portion of the hook and loop fastener extends along about an entire length of a side of each of the first and second fastening tabs that faces the respective first or second cuff.

23. The catheter cover device according to claim 21, wherein the fastening portion of the first cuff extends at least about one-quarter of the first circumferential length and the fastening portion of the second cuff extends at least about one-quarter of the second circumferential length.

24. The catheter cover device according to claim 1, wherein the folding portion of the first cuff extends at least about one-quarter of the first circumferential length and the folding portion of the second cuff extends at least about one-quarter of the second circumferential length.

25. The catheter cover device according to claim 1, wherein the first and second fastening tabs comprise waterproof fastening tabs.

26. The catheter cover device according to claim 25, wherein the first and second waterproof tabs having a larger width and length than the respective first and second cuffs.

27. The catheter cover device according to claim 25, wherein the first and second waterproof tabs comprise neoprene.

28. The catheter cover device according to claim 25, wherein the length of the first and second waterproof tabs permits the wrapping of the waterproof bands around a fully extended first or second opening, respectively, at least two times.

29. The catheter cover device according to claim 25, wherein the first and second waterproof tabs have fastening devices secured thereto to fasten to a backside of the respective waterproof tabs to hold the waterproof tabs in a wrapped position.

30. An adjustable IV catheter cover device comprising:
a sleeve defining a cavity therethrough, the sleeve having a length and a first end and a second end and the sleeve defining an access opening that extends along at least a portion of the length of the sleeve between the first end and the second end;
a first cuff disposed to the sleeve at the first end and defining an edge of a first opening leading into the cavity, the first cuff having an elastic portion, a fastening portion disposed next to a first end of the elastic portion of the first cuff and a folding portion disposed between the elastic portion and fastening portion of the first cuff;
a first fastening tab secured to the first cuff at a second end of the elastic portion of the first cuff between the folding portion of the first cuff and the elastic portion of the first cuff, the first fastening tab configured to be engageable with the fastening portion of the first cuff to adjust the size of the first opening;
a second cuff disposed to the sleeve at the second end and defining a second opening leading into the cavity, the second cuff having an elastic portion, a fastening portion disposed next to an end of the elastic portion of the second cuff and a folding portion disposed between the elastic portion and fastening portion of the second cuff;
a second fastening tab secured to the second cuff at a second end of the elastic portion of the second cuff between the folding portion of the second cuff and the elastic portion of the second cuff, the second fastening tab configured to be engageable with the fastening portion of the second cuff to adjust the size of the second opening;
a first waterproof band secured to at least one of the first cuff or the sleeve, the waterproof band having a larger width and length than the first tab to permit wrapping around the first end of the sleeve after the first tab has been used to adjust the first opening to an extremity on which the sleeve has been placed, thereby providing a seal to prevent entry of water through the first end of the sleeve; and a second waterproof band secured to at least one of the second cuff or the sleeve, the waterproof band having a larger width and length than the second tab to permit wrapping around the second end of the sleeve after the second tab has been used to adjust the second opening to an extremity on which the sleeve has been placed, thereby providing a seal to prevent entry of water through the second end of the sleeve.

31. The catheter cover device according to claim 30, wherein the first and second waterproof bands have fastening devices secured thereto to hold the bands in a wrapped position.

32. The catheter cover device according to claim 31, wherein the first and second waterproof bands comprise neoprene.

33. The catheter cover device according to claim 30, wherein the length of the first and second waterproof bands permits the wrapping the waterproof bands around a fully extended first or second opening, respectively, at least two times.

* * * * *